US012246126B2

(12) United States Patent
Fecteau (10) Patent No.: US 12,246,126 B2
(45) Date of Patent: Mar. 11, 2025

(54) POWDER SPRAY DISPENSER FOR COMMINUTED ECM

(71) Applicant: Cook Biotech Incorporated, West Lafayette, IN (US)

(72) Inventor: Christopher Fecteau, Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 1382 days.

(21) Appl. No.: 16/804,839

(22) Filed: Feb. 28, 2020

(65) Prior Publication Data

US 2020/0276399 A1 Sep. 3, 2020

Related U.S. Application Data

(60) Provisional application No. 62/812,192, filed on Feb. 28, 2019.

(51) Int. Cl.
*A61M 11/00* (2006.01)
*A61K 9/14* (2006.01)
(Continued)

(52) U.S. Cl.
CPC ............. *A61M 11/008* (2014.02); *A61K 9/14* (2013.01); *A61L 2/206* (2013.01);
(Continued)

(58) Field of Classification Search
CPC .......... A61M 11/008; A61M 2202/064; A61M 2202/095; A61M 2205/75;
(Continued)

(56) References Cited

U.S. PATENT DOCUMENTS 3,223,289 A * 12/1965 Bouet ............... B05B 11/00446
401/153
5,196,185 A 3/1993 Silver et al.
(Continued)

OTHER PUBLICATIONS

Cellerate Activated Collagen Powder. Datasheet [online]. Wound Care Innovations, LLC, 2003 [retrieved on Feb. 26, 2019]. Retrieved from the Internet: <URL: www.lifestylemedsupply.com/cellerate-activated-collagen-powder-1-gm-sold-by-box-of-24.html>.
(Continued)

*Primary Examiner* — Jessica Arble
*Assistant Examiner* — Nhu Q. Tran
(74) *Attorney, Agent, or Firm* — Woodard, Emhardt, Henry, Reeves & Wagner, LLC (57) ABSTRACT

Disclosed are powder spray dispensing devices for comminuted extracellular matrix powder materials, and terminally sterilized products for providing such devices, as well as related methods for manufacture and use. A powder spray dispensing device can include a squeeze pump bottle having a bottle body defining a bottle opening and an interior chamber. A dry collagenous extracellular matrix material powder is received in the interior chamber of the squeeze pump bottle, and a cap is fitted over the bottle opening. The cap has a dispensing spout fluidly communicating with the bottle opening and having a spout lumen, desirably of decreasing diameter in a direction extending away from the bottle opening. Amounts of the dry, comminuted collagenous extracellular matrix material powder are ejectable as a powder spray out (51) Int. Cl.
*A61L 2/20* (2006.01)
*A61L 27/36* (2006.01)
*B05B 11/04* (2006.01)
*B65B 55/02* (2006.01)

(52) U.S. Cl.
CPC ........ *A61L 27/3633* (2013.01); *B05B 11/041* (2013.01); *B65B 55/02* (2013.01); *A61L 2202/181* (2013.01); *A61L 2202/21* (2013.01); *A61L 2430/34* (2013.01); *A61M 2202/064* (2013.01); *A61M 2202/095* (2013.01); *A61M 2205/75* (2013.01); *A61M 2207/10* (2013.01)

(58) Field of Classification Search
CPC ............ A61M 2207/10; A61M 35/003; A61M 2209/06; A61K 9/14; A61L 2/206; A61L 27/3633; A61L 2202/181; A61L 2202/21; B05B 11/041; B65B 55/02; A61J 1/10; A61J 1/1412; A61J 1/1468; A61J 16
See application file for complete search history.

(56) References Cited

U.S. PATENT DOCUMENTS

| | | |
|---|---|---|
| 2003/0012741 A1 | 1/2003 | Furlan et al. |
| 2014/0133785 A1* | 5/2014 | Diviesti ................ B65B 61/182 |
| | | 383/102 |
| 2016/0114003 A1 | 4/2016 | Gennari et al. |
| 2016/0310542 A1 | 10/2016 | McPherson |
| 2020/0268607 A1* | 8/2020 | Gobbi Frattini .......... A61J 1/10 |

OTHER PUBLICATIONS

Gilbert et al., "Production and Characterization of ECM Powder: Implications for Tissue Engineering Applications", Biomaterials (2005), pp. 1431-1435, issue/vol. 26.

Wound Care Stimulen Collagen Powder. Datasheet [online]. RehabMart, 1998 [retrieved on Feb. 26, 2019]. Retieved from the Internet: <URL:www.rehabmart/products/wound-care-stimulen-collagen-powder-33393.html>.

* cited by examiner

POWDER SPRAY DISPENSER FOR COMMINUTED ECM

CROSS REFERENCE TO RELATED APPLICATION

This application claims the benefit of U.S. Provisional Application Ser. No. 62/812,192 filed Feb. 28, 2019, which is hereby incorporated by reference.

BACKGROUND

Aspects of the present disclosure relate to extracellular matrix (ECM) products and their administration to patients, and in particular forms to powder-form ECM products that can be applied to treat wounds or other damaged patient tissue. As further background, regenerative medicine has made significant advances in the past two decades. Naturally derived ECM materials have been commercialized and have been used to treat topical wounds and as internally implanted materials in patients. A limited number of applications of these ECM materials have involved applying to a patient a powder-form ECM. Powder forms can present difficulties in manufacture, handling, application and other areas. Accordingly, there are needs for improved and alternative products, manufacturing processes, and uses of powder-form ECMs. In some of its aspects, the present disclosure is addressed to these needs.

SUMMARY

In one aspect, the present disclosure relates to an article of manufacture that includes a sealed pouch having a first sterile barrier film defining an interior volume of the sealed pouch, the first sterile barrier film being permeable to humidified ethylene oxide gas. The article also includes a squeeze pump bottle received in the interior volume of the sealed pouch, the squeeze pump bottle having a bottle body impermeable to humidified ethylene oxide gas, the bottle body defining an interior chamber and a bottle opening. A second sterile barrier film seals the bottle opening and is permeable to humidified ethylene oxide gas. A dry, comminuted collagenous extracellular matrix material powder is received in the interior chamber of the squeeze pump bottle. A cap is also cap received in the interior volume of the sealed pouch and is attachable to the squeeze pump bottle to position the cap over the bottle opening (including after removal or puncture of the second barrier film). The cap has a dispensing spout defining a spout lumen terminating in a spout opening. Amounts of the dry, comminuted collagenous extracellular matrix material powder are ejectable as a powder spray out of the spout opening by a pumping inward deflection of at least one wall portion of the squeeze pump bottle that causes a gas pressure impulse to travel from the interior chamber of the squeeze pump bottle through the spout lumen and out the spout opening.

In a further aspect, the present disclosure relates to a device for dispensing a dry, comminuted collagenous extracellular matrix powder. The device includes a squeeze pump bottle having a bottle body defining a bottle opening and an interior chamber. A dry, comminuted collagenous extracellular matrix material powder is received in the interior chamber of the squeeze pump bottle. A cap is attached to the bottle and positioned over the bottle opening. The cap has a dispensing spout fluidly communicating with the bottle opening, the dispensing spout defining a spout lumen and a spout opening. Amounts of the dry collagenous extracellular matrix material powder are ejectable as a powder spray out of the spout opening by a pumping inward deflection of at least one wall portion of the squeeze pump bottle that causes a gas pressure impulse to travel from the interior chamber of the squeeze pump bottle through the spout lumen and out the spout opening.

In a still further aspects, the present disclosure relates to methods of manufacturing, and methods of using, articles of manufacture and dispensing devices as discussed above and elsewhere herein.

Additional aspects and embodiments, as well as features and advantages thereof, will be apparent to persons of skill in the relevant field from the descriptions herein.

DETAILED DESCRIPTION

Reference will now be made to certain embodiments and specific language will be used to describe the same. It will nevertheless be understood that no limitation of the scope of the disclosure is thereby intended, such alterations and further modifications, and such further applications of the principles as described herein being contemplated as would normally occur to one skilled in the art to which the invention relates.

As disclosed above, certain aspects of the present disclosure relate to spray dispensers for spray application of dry, comminuted extracellular matrix (ECM) powder products and to sterile products containing such spray dispensers or containing elements for assembly of such spray dispensers, and related methods of use and manufacture. In highly beneficial aspects, it has been discovered that dry, comminuted ECM powder products with relatively large particle sizes and where the particles are characterized by having an exterior distribution of exposed individualized fibers can be effectively spray dispensed as a forced stream of dispersed dry particles by squeeze pump action from squeeze pump bottles having a dispensing spout defining a lumen terminating in a spout orifice. The large particle size can contribute to effective coating or matting of the particles onto regions of damaged tissue, such as a topical wound, and also to providing beneficial extended ECM scaffold domains when applied to the damaged tissue, thus preserving regenerative properties of the ECM material.

Figure 1:
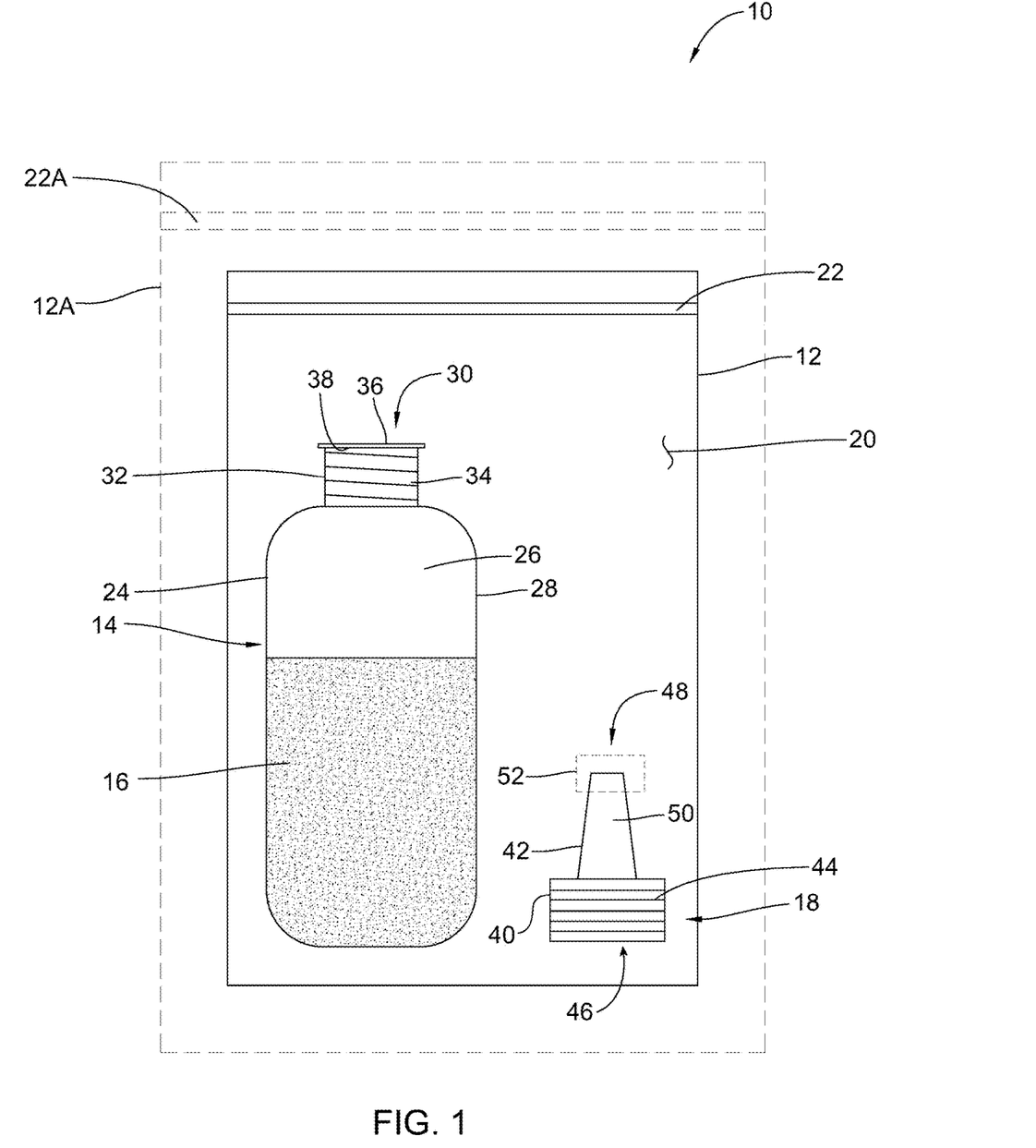
FIG. 1 provides a plan view of one embodiment of an article of manufacture of the present disclosure.

With reference to FIG. 1, shown is one embodiment of a medical article of manufacture or product 10 containing elements for assembly of a spray dispenser for a dry, comminuted ECM powder material. Sterilized medical product 10 includes a pouch 12 or other suitable medical package and, sealed within an interior of the pouch 12, a pre-filled squeeze pump bottle 14 containing a dry, comminuted ECM powder material 16, and a dispensing cap 18 attachable to the bottle 14.

The pouch 12 includes a flexible sterile barrier film 20, for example a Tyvek® film (a film of spun polyethylene fibers) defining a sealed interior. The seal can include a seal region 22 created after insertion of the pre-filled squeeze bottle 12 and cap 18 into the pouch, for example by heat sealing the film, and/or by adhesive, and/or by other suitable materials or techniques. It is also contemplated that pouch 12 can in some embodiments itself be sealed into a second pouch 12A (shown in phantom) having its own seal region 22A, providing a sterilized double pouch configuration.

The squeeze pump bottle 14 has a bottle body 24, which will typically be comprised of a polymeric material, for example in some embodiments a polyethylene plastic material. The bottle body 24 defines an interior chamber 26, which contains the dry, comminuted ECM powder material. Desirably, as shown in FIG. 1, the interior chamber 26 is only partially filled with the ECM powder material 16, leaving an unfilled space within the chamber 26 adjacent to the volume of ECM powder material 16, e.g. thereabove. In this manner, the powder material 16 can be caused to flow within chamber 26 by manipulation of the bottle 14, which facilitates charging actions that position amounts of the ECM powder 16 in or near the dispensing spout of cap 18 as discussed further below.

The bottle body 24 has squeezable bottle walls 28 that can be squeezed to deflect them inwardly and that resiliently return to their original (non-squeezed, or relaxed) shape after cessation of the squeezing force. In this manner, a squeeze pump action can be applied to the bottle to force a gas (e.g. air) stream out of the opening of the bottle and then out of a dispensing spout of the cap 18, as discussed further below.

The bottle body 34 defines a bottle opening 30 that can provide access to the chamber 26, and a bottle neck 32 having an external thread 34 for threaded attachment of cap 18. The pre-filled squeeze pump bottle 14 has a sterile barrier bottle seal film 36 (e.g. a Tyvek® film material as discussed above) that sealingly covers the bottle opening 30. The bottle seal film 36 is preferably permeable to humidified ethylene oxide gas, for sterilization purposes. The bottle seal film 36 can be removably attached to the bottle neck 32, for example by a suitable adhesive. For purposes of removal by peeling, the bottle seal film 36 can include a portion 38 that extends beyond and overhangs the bottle neck 32 to provide a grip that a user can grasp to peel the film 36 from the neck 32 to expose the bottle opening 30, e.g. for attachment of the cap 18 to the bottle 14. The bottle body can be of any suitable size, with bottles defining interior chambers with a fluid volume capacity of about 30 ml to about 120 ml being employed in some aspects. The amount of ECM powder material in the interior chamber of the bottle may also vary, for example in some forms having a mass in the range of about 100 mg to about 2000 mg.

The dispensing cap 18 includes a thread body portion 40 and a dispensing spout 42. Thread body portion 40 defines an internal thread 44 that cooperates with external thread 34 of the squeeze pump bottle 12 for threaded attachment. Dispensing cap 18 defines a fluid path including an entry opening 46 and a spout opening 48. Typically, entry opening 46 will have a larger cross-sectional area than that of the spout opening 48. The spout 42 defines a lumen 50, desirably a lumen having a diminishing diameter (e.g. staggered or continuous) extending in a direction from the entry opening 46 to the spout opening 48 (i.e. in a direction away from the bottle body 24 when attached thereto). Lumen 50 can be generally conical in shape. The exterior shape of the spout 42 can also be generally conical, and the spout 42 can have spout walls that converge toward one another in a direction from the entry opening 46 to the spout opening 48. Optionally, a spout cap 52 can be removably fitted over the spout opening 48, for example friction fitted thereover. The cross-sectional area of the spout opening 48 can in some aspects be in the range of about 0.25 mm to about 5 mm or about 0.5 mm to about 3 mm (as manufactured, prior to any trimming). Where the lumen 50 has a diminishing diameter as discussed above, the spout 42 can be trimmed along its length to provide a newly created spout opening having a cross-sectional diameter greater than that of the manufactured, untrimmed opening, for example about 5% to about 300% greater in some forms.

Suitable squeeze pump bottles and dispensing caps as described herein can be manufactured using known methods and materials, or can be obtained commercially. Illustratively, suitable squeeze pump bottles, such as so-called Boston round bottom bottles, and dispensing "yorker" caps, are commercially available from Qorpak, Inc. (Bridgeville, PA, USA).

Figure 2:
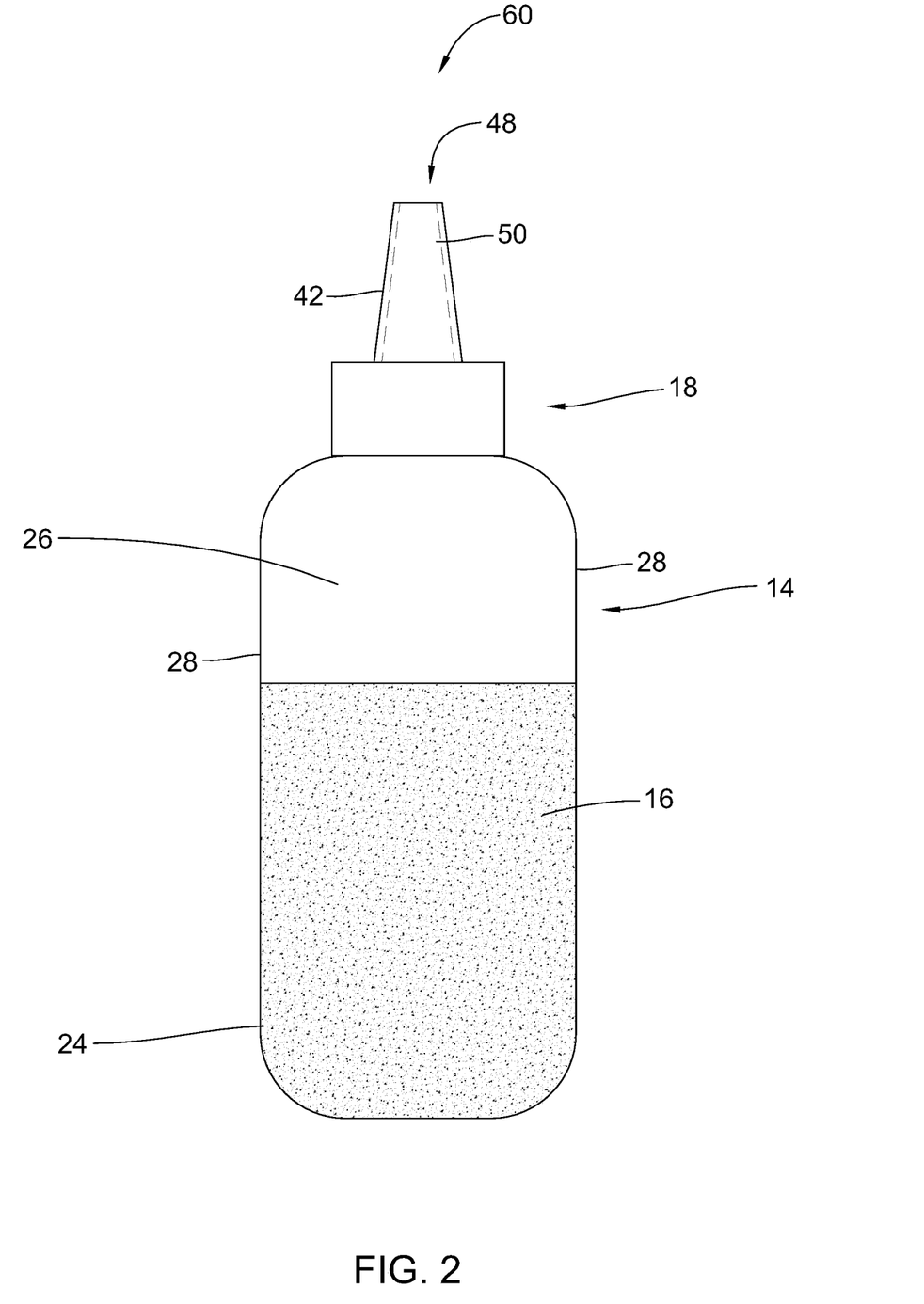
FIG. 2 provides a perspective view of one embodiment of a powder spray dispenser for a dry, comminuted ECM powder of the present disclosure.

Referring now to FIG. 2, shown is an assembled spray dispenser 60 for a dry, comminuted ECM powder material. For example, spray dispenser 60 can be assembled from the product 10 of FIG. 1 by opening the sealed pouch(es), removing the pre-filled bottle 14 and cap 18 from the pouch(es), separating the film 36 from the bottle body 24, and threading the cap 18 onto the bottle neck 32 using cooperating threads 44 and 34, respectively. This can be done in a sterile fashion and/or environment, for example in an operating room in which a patient is to be treated with the ECM powder material 16.

In use, the dry, comminuted ECM powder can be dispensed from the interior chamber 26 of the bottle body 24 by a squeeze pump action (e.g. manually by a hand of a user). In this regard, the bottle walls 28 can be squeezed to deflect them inwardly, e.g. to cause opposed wall portions to deflect inwardly toward one another. This forces a stream of gas (e.g. air) out of the opening 30 of the bottle, through the lumen 50 defined within the dispensing spout 42, and out of the spout opening 48. Easing or cessation of the squeezing force causes the bottle walls 28 to resiliently return toward or to their original (non-squeezed, or relaxed) shape and draw gas (e.g. air) into the interior chamber 26, whereafter a squeezing force can be reapplied to bottle walls 28 to force another stream of gas (e.g. air) out of the opening 30 of the bottle, through the lumen 50 defined within the dispensing spout 42, and out of the spout opening 48. This process can be repeated multiple times to provide multiple impulses or streams of gas travelling from interior chamber 26 and exiting the spout opening 48. Amounts of the dry, comminuted ECM powder material 16 caught up in these impulses of gas can be ejected from the spout opening 48 as a forced spray of dispersed, dried ECM powder particles.

The dispensing of the dry, comminuted ECM powder material 16 can be facilitated by manipulating (e.g. shaking and/or tilting) the spray dispenser 60 to charge a portion of, or at least a portion of, the powder material 16 to a position within interior chamber 26 adjacent the cap 18 and/or in the cap 18 such as into the lumen 50 of the spout 42. The bottle walls 28 can then be squeezed to deflect them inwardly to force a stream of gas (e.g. air) out of the opening 30 of the bottle, through the lumen 50 defined within the dispensing spout 42, and out of the spout opening 48. At least a portion of, and potentially all of, the charge of the ECM powder material 16 is thereby taken up in the air or gas stream impulse and spray dispensed from the spout opening 48. Repeated charging and pumping actions as discussed above can then be used to spray dispense additional amounts of the ECM powder material 16 from the spout opening 16. For these purposes, it has been found that ECM powder materials 16 of preferred physical parameters as described herein, when moved into spaces of decreasing volume for charging, are capable of forming a gathered or packed volume of ECM powder that resists falling downwardly back into chamber 26 under the forces of gravity (e.g. when the spout 18 is pointed upwardly), and instead remaining charged and staged for squeeze pump dispensing from spout opening 48 as discussed herein. The impulse of air or other gas from the squeeze pump action can disrupt the charged, gathered or packed volume of ECM powder 16 and disperse the particles of the ECM powder 16 as it is spray ejected from the spout opening 48. It has also been found that the driving impulse of air or gas from the pumping action can pass through an unejected volume of ECM powder and eject volumes of ECM powder closer to the spout opening 48.

The spray of dry, comminuted ECM powder 16 can be applied to treat tissue of a human patient or veterinary patient such as a dog, cat or horse. For example, the material 16 can be spray applied to treat damaged tissue, such as that of a topical wound of a patient. Such wounds may include, for example, partial and full thickness wounds, cuts, scrapes, abrasions, lacerations, skin tears, tunneled and undermined wounds, skin donor sites, degloving injuries, post laser surgery, post-Moh's surgery, distal limb/foot wound dehiscence, burns, ulcers (e.g. chronic ulcers or pressure ulcers), or others. Other regions of damaged tissue, including those located internally in the patient, can also be treated. The applied dry, comminuted ECM powder material can contact and stick to the wound or other damaged tissue, which can be facilitated by moisture applied to and/or naturally occurring in the damaged tissue. The ECM powder materials described herein are capable of beneficially coating and in preferred aspects associating to form a wet matt of ECM powder particles on the wound or other damaged tissue.

Terminally sterilized products of the present disclosure can be provided by assembling the pouch(es) and interior pouch contents as described in FIG. 1 (potentially along with other materials or devices), and subjecting the sealed pouch(es) to a sterilizing agent, especially humidified ethylene oxide gas. In other embodiments herein, any suitable sealed, sterile barrier container or package that is permeable to humidified ethylene oxide gas (or any other sterilizing agent used) can be employed in the place of one or both of the pouches 12 and 12A. In using humidified ethylene oxide gas in preferred embodiments, the gas can sufficiently penetrate both the pouch(es) 12, 12A (or other sealed container(s)) and the capping film 36 to sterilize all of the pouch(es) contents, including the pre-filled ECM powder material 16. In this manner, the ECM powder 16 need only be exposed to the sterilizing agent a single time as contained within the prefilled bottle 14 within the pouch(es), which can help to preserve bioactivity in dry, comminuted ECM powder materials that include one or more growth factors from a source tissue as discussed herein, since repeated exposures can diminish the measurable bioactivity of the growth factor(s).

In other aspects, other sterilizing agents, such as gamma, e-beam, or other sterilizing radiation, can be used to form the terminally sterilized products. For these purposes, the bottle body 24 can be made of material that is permeable to the sterilent energy. As well in these embodiments, the cap 18 can optionally be pre-attached to the bottle body 24 and a removable sterile seal (e.g. film) provided over spout opening 48 during the terminal sterilization. This latter configuration can also be used when using humidified ethylene oxide gas so long as at least a portion of the bottle/cap assembly (e.g. a sterile barrier film over spout opening 48) is permeable to the humidified ethylene oxide gas so that the ECM powder material 16 is rendered sterile. In still further embodiments, sterile or aseptic handling and filling techniques can be used to provide the dry, comminuted ECM powder material 16 in the spray dispenser 60, and the dispenser 60 can then be sterilely sealed and/or sealed within an outer sterile pouch or other container. These and other techniques for providing a medically suitable, packaged dry, comminuted ECM powder material are contemplated in embodiments of the present disclosure.

The dry, comminuted ECM powder materials herein can be prepared by comminuting one or more intact segments of a decellularized collagenous ECM tissue membrane. Suitable materials for use in any of the embodiments herein can be provided by membranous collagenous ECM materials. For example, suitable membranous ECM materials include as examples those comprising submucosa, renal capsule membrane, dermal collagen, dura mater, pericardium, fascia lata, serosa, subserous fascia, amnion, peritoneum or basement membrane layers, including liver basement membrane. These materials can be sourced from animals, and especially mammals such as bovine, ovine, or porcine mammals. Suitable submucosa materials for these purposes include, for instance, intestinal submucosa including small intestinal submucosa, stomach submucosa, urinary bladder submucosa, and uterine submucosa. These or other ECM materials can be characterized as membranous tissue layers harvested from a source tissue and decellularized. These membranous tissue layers can have a porous matrix comprised of a network of collagen fibers, wherein the network of collagen fibers preferably retains an inherent network structure from the source tissue. In particular aspects, collagenous matrices comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source, and decellularizing the matrix before or after such delaminating. For additional information as to some of the materials useful in the present invention, and their isolation and treatment, reference can be made, for example, to U.S. Pat. Nos. 4,902,508, 5,554,389, 5,993,844, 6,206,931, 6,099,567, 8,541,372 and 9,044,455.

Submucosa-containing or other ECM tissue, when used in the invention, is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present invention.

Decellularized ECM materials for use in the invention can be prepared by processes that decrease the content of undesired components of the source tissue such as cells, nucleic acid, lipids and/or immunoglobulins such as IgA, while retaining substantial levels of desired components from the source tissue such as growth factor(s) (e.g. Fibroblast Growth Factor-2), proteoglycans and/or glycosaminoglycans (GAGs). Such treatments can be performed with detergent, basic medium, liquid organic solvent, and/or disinfecting solution, for example as described in U.S. Pat. No. 8,192,763 issued Jun. 5, 2012, the disclosure of which is specifically incorporated herein by reference in its entirety.

Submucosa-containing or other membranous ECM tissue material may retain one or more growth factors native to the source tissue for the tissue material, such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other bioactive agents native to the source tissue, such as but not limited to proteins, glycoproteins, proteoglycans, and glycosaminoglycans. For example, ECM materials may include native heparin, native heparin sulfate, native hyaluronic acid, native fibronectin, native cytokines, and the like. Thus, generally speaking, a submucosa or other ECM material may retain one or more native bioactive components from the source tissue that induce, directly or indirectly, a cellular response such as a change in cell morphology, proliferation, growth, protein or gene expression.

Submucosa-containing or other ECM materials can be derived from any suitable organ or other tissue source, usually sources containing connective tissues. The ECM materials processed for use in the invention will typically be membranous tissue layers that include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

A submucosa-containing or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Comminuted ECM powder materials for use herein can be prepared by comminuting single layers or laminates including two or more individual layers of membranous ECM material (e.g., 2 or more layers bonded together). The comminution process can be conducted, for example, by grinding or milling processes with wet or dry material, including for example cryogrinding or cryomilling processes. The direct resulting comminuted ECM material can optionally be screened or sieved to capture a size fraction or fractions that can be used for a comminuted ECM powder material herein. However, in some embodiments, all or essentially all (e.g. greater than 95% or greater than 98%) of the total product of the milling or grinding process can be successfully used in the spray dry dispensing products and processes described herein, and can provide the physical and performance properties discussed above.

Figure 3:
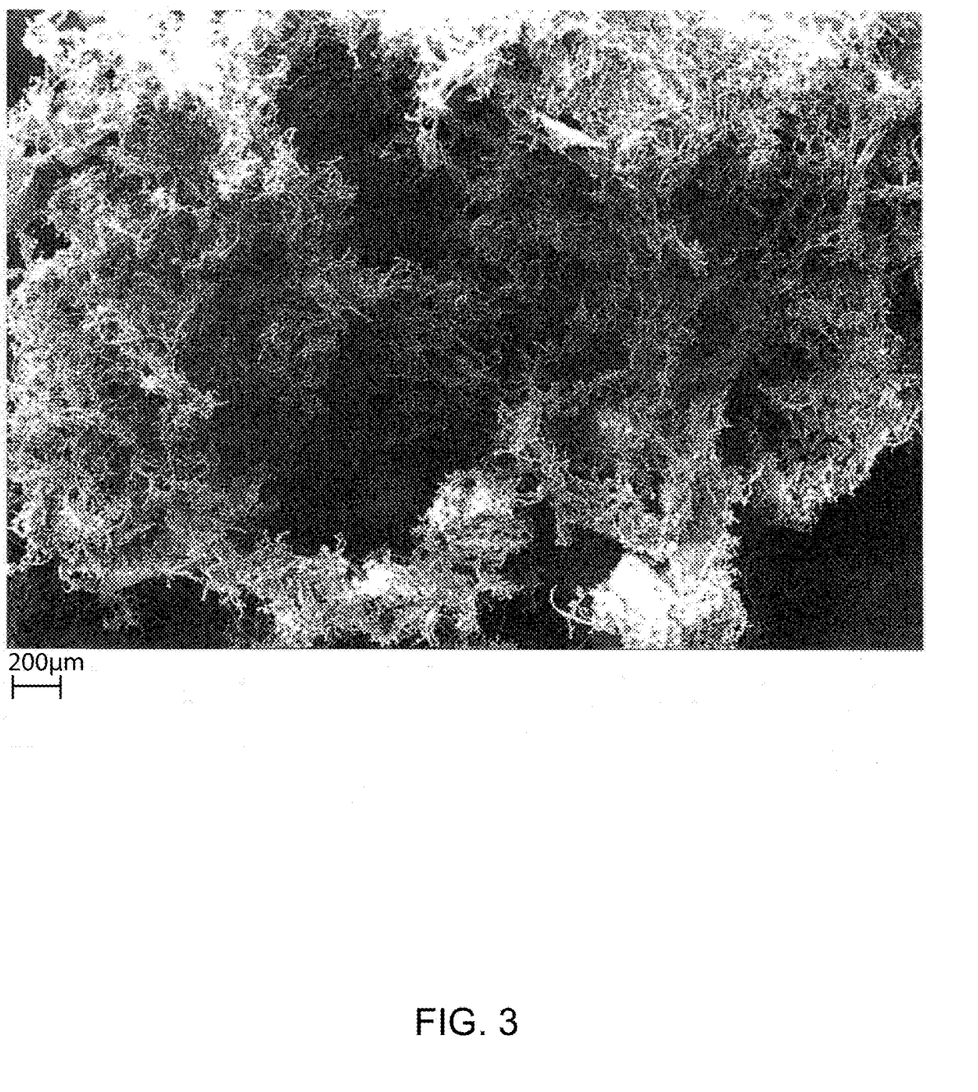
FIG. 3 provides a magnified digital image of an exemplary comminuted ECM powder material.

Comminution of larger ECM material segments to produce comminuted ECM powders can produce ECM powder particles having beneficial physical characteristics for use in the spray dispensing products and processes herein. Illustratively, as shown in the digital image of FIG. 3, particles of a comminuted ECM powder can have an exterior distribution of exposed individualized fibers. This can contribute to providing beneficial behavioral properties to the ECM powder material for its use in gas-driven dry spraying from spray dispensers as described herein as well as in covering damaged tissue to which the powder material is applied.

The comminuted ECM powder can also have other attributes enabling beneficial handling and performance properties of products and processes herein. In some forms, the comminuted ECM powder material has an mean particle diameter of greater than about 75μ, or greater than about 100μ, and typically in the range of about 75μ to about 200μ and more preferably in the range of about 75μ to about 150μ. In addition or alternatively, the comminuted ECM powder material has a mode of about 100μ or greater, or about 115μ or greater, and in some forms in the range of about 100μ to about 250μ. In addition or alternatively, the comminuted ECM powder material can be characterized by at least 50% by volume of its particles having a maximum diameter of greater than about 75μ, or greater than about 90μ; and/or less than 10% by volume of its particles having a maximum diameter of less than about 10μ, or less than about 20μ. These particle sizing determinations can be made by known light scattering based techniques, such as laser diffraction particle sizing.

Particle size analysis on three illustrative lots of comminuted ECM (SIS in this case) useful herein provided the results in Table 1 below.

TABLE 1

| Measure | Particle Diameter (μm) | | |
|---|---|---|---|
| | Lot 1 | Lot 2 | Lot 3 |
| $D_{10}$ | 23.6 | 20.8 | 20.4 |
| $D_{50}$ | 105.7 | 94.4 | 94.0 |
| $D_{90}$ | 216.8 | 201.3 | 204.4 |
| $D_{100}$ | 317.7 | 267.3 | 300.0 |
| $D_{mode}$ | 177.3 | 199.0 | 133.0 |
| $D_{mean}$ | 113.7 | 103.0 | 103.8 |

Figure 4:
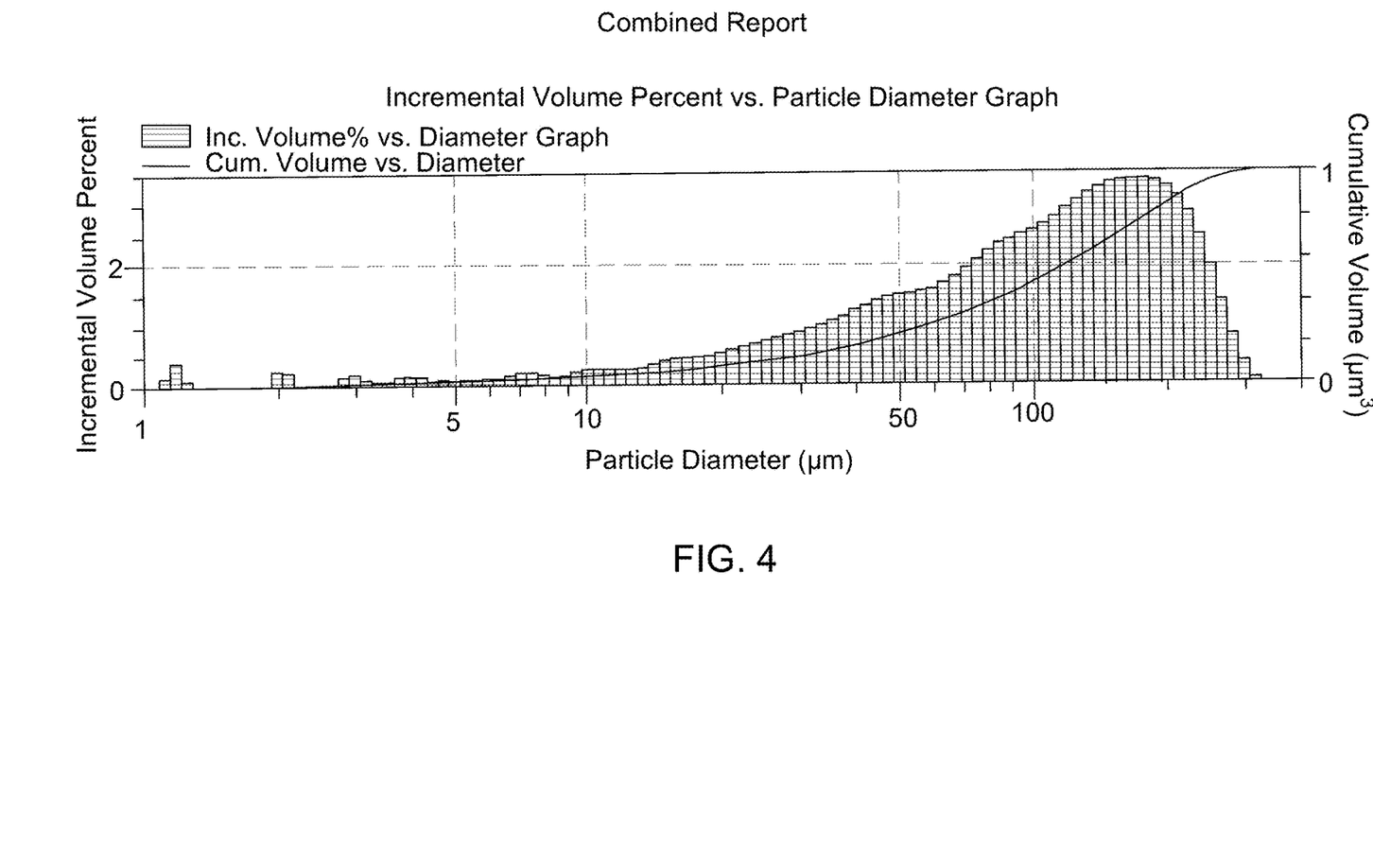
FIG. 4 provides a combined graph showing incremental volume percent versus particle diameter and showing cumulative volume versus particle diameter for one exemplary dry, comminuted ECM powder.

As will be understood, the $D_{10}$ values denote the particle diameter at which 10% of the particles by volume have a smaller particle diameter. Correspondingly, the $D_{50}$, $D_{90}$ and $D_{100}$ values denote the particle diameter at which 50% by volume, 90% by volume, or 100% by volume, respectively, of the particles have a smaller particle diameter. $D_{mode}$ denotes the mode of the particles of the product, and $D_{mean}$ denotes the mean (i.e. average) diameter of the particles of the product. Relatedly, provided in FIG. 4 is a graph showing incremental volume percent vs. particle diameter and cumulative volume vs. diameter for Lot 1 reported in Table 1 above.

The comminuted ECM powder can be provided in its dry form by drying before and/or after comminuting a larger ECM material (e.g. sheet) to a powder form. In certain aspects, a dry ECM sheet material can be comminuted to provide a dry, comminuted ECM powder product, which is used herein. In other forms, the ECM sheet material can contain frozen or liquid water during the comminution process, and the formed wet powder material can then be dried to provide the dry powder for use in the products and processes disclosed herein. Any suitable drying technique, or combination of techniques, can be used, including air drying, oven drying, vacuum drying, and/or lyophilization. In preferred forms, the dry, comminuted ECM powder is a lyophilized ECM powder.

The dry, comminuted ECM powder material can optionally be included in combination with other particulate materials, including for example particulate active agents such as drugs, other particulate scaffolding materials, particulate flow additives, or other particulate components. In preferred forms, the contents of the spray dispenser consist of or consist essentially of (e.g. are constituted greater than about 98% by weight of) the comminuted ECM powder material.

The uses of the terms "a" and "an" and "the" and similar references in the context of describing the invention (especially in the context of the following claims) are to be construed to cover both the singular and the plural unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and the foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. An article of manufacture, comprising:
   a sealed pouch having a first sterile barrier film defining an interior volume of the sealed pouch, the first sterile barrier film being permeable to humidified ethylene oxide gas;
   a squeeze pump bottle received in the interior volume of the sealed pouch, the squeeze pump bottle having a bottle body impermeable to humidified ethylene oxide gas, the bottle body defining an interior chamber and a bottle opening, wherein a second sterile barrier film seals the bottle opening, the second sterile barrier film permeable to humidified ethylene oxide gas, and wherein a dry, comminuted collagenous extracellular matrix material powder is received in the interior chamber of the squeeze pump bottle; and
   a cap received in the interior volume of the sealed pouch and attachable to the squeeze pump bottle to position the cap over the bottle opening after removal or puncture of the second barrier film, the cap having a dispensing spout defining a spout lumen terminating in a spout opening;
   wherein amounts of the dry, comminuted collagenous extracellular matrix material powder are ejectable as a powder spray out of the spout opening by a pumping inward deflection of at least one wall portion of the squeeze pump bottle that causes a gas pressure impulse to travel from the interior chamber of the squeeze pump bottle through the spout lumen and out the spout opening.

2. The article of manufacture of claim 1, wherein the dry, comminuted collagenous extracellular matrix material powder has an average particle size in the range of 75μ to 200μ.

3. The article of manufacture of claim 1, wherein particles of the dry, comminuted collagenous extracellular matrix material powder have an external distribution of exposed individualized fibers.

4. The article of manufacture of claim 1, wherein the dry, comminuted collagenous extracellular matrix powder is provided as a volume that occupies no more than 50% of a volume of the interior chamber of the squeeze pump bottle.

5. The article of manufacture of claim 1, wherein the dry, comminuted collagenous extracellular matrix material powder comprises growth factors, proteoglycans and glycosaminoglycans native to an animal source tissue for the dry, comminuted collagenous extracellular matrix material powder.

6. The article of manufacture of claim 5, wherein the dry, comminuted collagenous extracellular matrix powder has a mean particle diameter of greater than 75μ.

7. The article of manufacture of claim 5, wherein the dry, comminuted ECM powder has a particle mode of 100μ or greater.

8. The article of manufacture of claim 5, wherein the dry, comminuted collagenous extracellular matrix powder has a particle mode in the range of 100μ to 250μ.

9. The article of manufacture of claim 5, wherein at least 50% by volume of the particles of the dry, comminuted collagenous extracellular matrix powder have a maximum diameter of greater than 75μ.

10. A method for manufacturing a medical product, comprising:
    providing an article of manufacture according to claim 1; and
    subjecting the article of manufacture to humidified ethylene oxide gas.

11. The article of manufacture of claim 1, wherein the spout lumen has a decreasing diameter in a direction extending away from the bottle opening when the cap is attached to the bottle.

12. The article of manufacture of claim 1, wherein the cap is received in the interior volume of the sealed pouch separate from the squeeze pump bottle.

13. The article of manufacture of claim 1, wherein the dry, comminuted collagenous extracellular matrix powder has a mean particle diameter of greater than about 100μ.

14. The article of manufacture of claim 1, wherein the cap is received in the interior volume of the sealed pouch attached to the squeeze pump bottle.

15. The article of manufacture of claim 1, wherein at least 50% by volume of the particles of the dry, comminuted collagenous extracellular matrix powder have a maximum diameter of greater than 90μ.

16. The article of manufacture of claim 1, wherein less than 10% by volume of the particles of the dry, comminuted collagenous extracellular matrix powder have a maximum diameter of less than 20μ.

17. The article of manufacture of claim 1, wherein less than 10% by volume of the particles of the dry, comminuted collagenous extracellular matrix powder have a maximum diameter of less than 20μ.

18. The article of manufacture of claim 1, wherein the sealed pouch has been exposed to humidified ethylene oxide gas to sterilize the squeeze pump bottle, the dry, comminuted collagenous extracellular matrix material powder, and the cap.

19. The article of manufacture of claim 3, wherein the dry, comminuted collagenous extracellular matrix material powder has an average particle size in the range of 75μ to 200μ.

20. The article of manufacture of claim 19, wherein dry, comminuted collagenous extracellular matrix material powder has been prepared by comminuting one or more segments of a decellularized collagenous extracellular matrix tissue membrane.

21. The article of manufacture of claim 20, wherein the decellularized collagenous extracellular matrix tissue membrane comprises submucosa.

22. The article of manufacture of claim 21, wherein the decellularized collagenous extracellular matrix tissue membrane comprises intestinal submucosa, stomach submucosa, urinary bladder submucosa, or uterine submucosa.

23. The article of manufacture of claim 21, wherein the decellularized collagenous extracellular matrix tissue membrane comprises small intestinal submucosa.

* * * * *